United States Patent
Wojtysiak

(10) Patent No.: US 11,967,409 B2
(45) Date of Patent: Apr. 23, 2024

(54) MEDICAL DEVICE AUDIBLE AND VISUAL ALARM SYNCHRONIZATION

(71) Applicants: BAXTER INTERNATIONAL INC., Deerfield, IL (US); BAXTER HEALTHCARE SA, Glattpark (CH)

(72) Inventor: Slawomir Edward Wojtysiak, McHenry, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 282 days.

(21) Appl. No.: 17/237,629

(22) Filed: Apr. 22, 2021

(65) Prior Publication Data
US 2021/0335473 A1  Oct. 28, 2021

Related U.S. Application Data

(60) Provisional application No. 63/014,997, filed on Apr. 24, 2020.

(51) Int. Cl.
*G16H 20/17* (2018.01)
*A61M 5/142* (2006.01)
(Continued)

(52) U.S. Cl.
CPC ............ *G16H 20/17* (2018.01); *A61M 5/142* (2013.01); *G16H 40/63* (2018.01); *G16H 40/67* (2018.01);
(Continued)

(58) Field of Classification Search
CPC ........ G16H 20/17; G16H 40/67; G16H 40/63; G16H 20/10; G16H 40/00; G16H 40/60; A61M 5/142; A61M 2205/18; A61M 2205/3553; A61M 2205/3561; A61M 2205/581; A61M 2205/582; A61M 2205/583; A61M 5/1407; A61M 5/1413; A61M 2205/3584; A61M 2205/50; A61M 2205/52; A61M 2205/6072; G06F 3/1423; G06F 3/00; G06F 3/14; G06F 1/12; G06F 21/6245; G09G 5/12; G09G 2350/00;
(Continued)

(56) References Cited

U.S. PATENT DOCUMENTS

2009/0177248 A1 * 7/2009 Roberts ............... G16H 40/67
607/60

FOREIGN PATENT DOCUMENTS

CA       2548290 C  * 10/2013   ............. G16H 40/20

* cited by examiner

*Primary Examiner* — James J Yang
*Assistant Examiner* — Anthony D Afrifa-Kyei
(74) *Attorney, Agent, or Firm* — K&L Gates LLP

(57) ABSTRACT

A system includes a server including a clock and a plurality of medical devices in network communication with the server. Each medical device includes at least one alarm mechanism and an internal clock. A first medical device of the plurality of medical devices is configured to receive a clock synchronization data from the server, update the internal clock of the first medical device based on the clock synchronization data, provide an alarm signal of a first type at a first time, and provide a subsequent alarm signal of the first type at a second time. The second time occurs at a predetermined interval from the first time. Additionally, the second time is the same time the alarm signal of the first type is provided by a second medical device of the plurality of medical device.

20 Claims, 3 Drawing Sheets

(51) Int. Cl.
*G16H 40/63* (2018.01)
*G16H 40/67* (2018.01)

(52) U.S. Cl.
CPC . *A61M 2205/18* (2013.01); *A61M 2205/3553* (2013.01); *A61M 2205/3561* (2013.01); *A61M 2205/581* (2013.01); *A61M 2205/582* (2013.01); *A61M 2205/583* (2013.01)

(58) Field of Classification Search
CPC ........... G09G 2354/00; G09G 2358/00; G09G 2370/02; G09G 2370/022; G09G 2380/08; H04L 67/1095; H04L 67/12; H04L 63/061; H04L 63/0876
See application file for complete search history.

MEDICAL DEVICE AUDIBLE AND VISUAL ALARM SYNCHRONIZATION

RELATED APPLICATIONS

This application claims the benefit of and priority to U.S. Provisional Patent Application No. 63/014,997 filed Apr. 24, 2020, entitled "MEDICAL DEVICE AUDIBLE AND VISUAL ALARM SYNCHRONIZATION", which is incorporated herein by reference in its entirety.

BACKGROUND

The present invention relates to medical devices, such as infusion pumps for the delivery of a medication to a patient. Generally, medical patients sometimes require precise delivery of either continuous medication or medication at set periodic intervals. Medical pumps have been developed to provide controlled drug infusion wherein the drug can be administered at a precise rate that keeps the drug concentration within a therapeutic margin and out of an unnecessary or possibly toxic range. Basically, the medical pumps provide appropriate drug delivery to the patient at a controllable rate, which does not require frequent attention.

Medical pumps may facilitate administration of intravenous therapy to patients both in and outside of a clinical setting. Outside a clinical setting, doctors have found that in many instances patients can return to substantially normal lives, provided that they receive periodic or continuous intravenous administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusion of drugs in solution over relatively short periods such as from 30 minutes to two hours. These conditions and others have combined to promote the development of increasingly lightweight, portable or ambulatory infusion pumps that can be worn by a patient and are capable of administering a continuous supply of medication at a desired rate, or providing several doses of medication at scheduled intervals.

Configurations of infusion pumps include elastomeric pumps, which squeeze solution from flexible containers, such as balloons, into IV tubing for delivery to the patient. Alternatively, spring-loaded pumps pressurize the solution containers or reservoirs. Certain pump designs utilize cartridges containing flexible compartments that are squeezed by pressure rollers for discharging the solutions. Infusion pumps utilizing syringes are also known wherein a drive mechanism moves a plunger of the syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls.

Several medical devices, such as infusion pumps, may be in the same area (e.g., same hospital room and associated with a single patient) and in some instances multiple infusion pumps may be arranged in a rack. Each of these medical devices may provide audible and visual alerts and alarms. Depending on the sound, tone, location, priority, and frequency of occurrence (e.g., how often the alarm sounds) of the alerts and alarms, the alerts may be difficult to distinguish from one another. Additionally, the alerts may be difficult to hear altogether based on interference from other sources (e.g., other lights and sounds), especially interference from the alerts from the other medical devices.

Multiple needs exist to enhance the hospital environment by reducing constant alarm noise (e.g., to reduce the stress of the patient and other visitors) while also minimizing interference between different alerts. Specifically, a need exists to synchronize alarms of the same type such that the alarms are more easily discernable to a user and also to reduce constant noise from alarms of the same type occurring at different frequencies. Another need exists to provide alarms of a different type or from a different location out-of-sync such that a user can more easily discern the type of alarm or the location of the alarm.

SUMMARY

The instant invention provides medical device systems and methods with synchronized audible and visual alerts/alarms. Alerts/alarms may be provided in-sync or out-of-sync with alerts/alarms from other medical devices based on the type of alarm and the location of the medical device.

Aspects of the subject matter described herein may be useful alone or in combination with one or more other aspects described herein. In a first aspect, which may be used with any other aspect described herein, a system includes a server including a clock and a plurality of medical devices in network communication with the server. Each medical device includes at least one alarm mechanism and an internal clock. A first medical device of the plurality of medical devices is configured to receive a clock synchronization data from the server, update the internal clock of the first medical device based on the clock synchronization data, provide an alarm signal of a first type at a first time, and provide a subsequent alarm signal of the first type at a second time. The second time occurs at a predetermined interval from the first time. Additionally, the second time is the same time the alarm signal of the first type is provided by a second medical device of the plurality of medical devices.

In a second aspect, which may be used with any other aspect described herein, the medical device is an infusion pump.

In a third aspect, which may be used with any other aspect described herein, a third medical device of the plurality of medical devices is configured to receive the clock synchronization data from the server, update the internal clock of the third medical device based on the clock synchronization data, provide an alarm signal of a second type at a third time, and provide a subsequent alarm signal of the second type at a fourth time. The fourth time occurs at a predetermined interval such that the subsequent alarm signal of the second type is out-of-sync with the alarm signal of the first type from the first medical device and the second medical device.

In a fourth aspect, which may be used with any other aspect described herein, clock synchronization data is provided through the Network Time Protocol (NTP).

In a fifth aspect, which may be used with any other aspect described herein, the alarm signal is one of an audible alarm, a visual alarm, and a tactile alarm.

In a sixth aspect, which may be used with any other aspect described herein, the audible alarm is provided by a speaker.

In a seventh aspect, which may be used with any other aspect described herein, the visual alarm is provided by an LCD display.

In an eight aspect, which may be used with any other aspect described herein, the visual alarm is provided by a LED.

In a ninth aspect, which may be used with any other aspect described herein, an infusion pump includes an internal clock, a display device configured to provide visual content, a speaker configured to provide audible content, and a processor in communication with the display and the speaker. The processor is configured to receive clock synchronization data from one of a server and another medical device, update the internal clock based on the clock synchronization data, provide an alarm signal at a first time from at least one of the display device and the speaker, and provide a subsequent alarm signal at a second time. Additionally, the second time occurs at a predetermined interval from the first time. The second time is the same time the alarm signal is provided by another infusion pump.

In a tenth aspect, which may be used with any other aspect described herein, clock synchronization data is provided through the Network Time Protocol (NTP).

In an eleventh aspect, which may be used with any other aspect described herein, the processor provides the alarm signal via the display device.

In a twelfth aspect, which may be used with any other aspect described herein, the processor provides the alarm signal via the speaker.

In a thirteenth aspect, which may be used with any other aspect described herein, the processor is further configured to provide an alarm signal of a second type at a third time, and provide a subsequent alarm signal of the second type at a fourth time. The fourth time occurs at a predetermined interval such that the subsequent alarm signal of the second type is out-of-sync with the alarm signal of the first type.

In a fourteenth aspect, which may be used with any other aspect described herein, a method includes receiving, by a medical device, clock synchronization data from a reference source. The method also includes updating, by the medical device, an internal clock based on the clock synchronization data. Additionally, the method includes providing, by the medical device, an alarm signal of a first type at a first time. The medical device also provides a subsequent alarm signal of the first type at a second time. The second time occurs at a predetermined interval from the first time, and the second time is the same time the alarm signal is provided by another medical device of the plurality of medical devices.

In a fifteenth aspect, which may be used with any other aspect described herein, the method further includes receiving, by a second medical device, the clock synchronization data from the server. Additionally, the second medical device updates an internal clock of the second medical device based on the clock synchronization data and provides an alarm signal of a second type at a third time. Additionally, the second medical device provides a subsequent alarm signal of the second type at a fourth time. The fourth time occurs at a predetermined interval such that the subsequent alarm signal of the second type is out-of-sync with the alarm signal of the first type.

In a sixteenth aspect, which may be used with any other aspect described herein, clock synchronization data is provided through the Network Time Protocol (NTP).

In a seventeenth aspect, which may be used with any other aspect described herein, the alarm signal is one of an audible alarm, a visual alarm, and a tactile alarm.

In an eighteenth aspect, which may be used with any other aspect described herein, the audible alarm is provided by a speaker.

In a nineteenth aspect, which may be used with any other aspect described herein, the visual alarm is provided by an LCD display.

In a twentieth aspect, which may be used with any other aspect described herein, the visual alarm is provided by a LED.

Therefore, it is a primary object of the invention to provide synchronized audible alarms between several medical devices.

It is another object of the invention to provide synchronized visual alarms between several medical devices.

It is yet another object of the invention to enhance the hospital environment by reducing constant alarm noise while also minimizing interference between different alarms.

It is another object of the present invention to reduce the stress to the patient and/or other visitors.

It is yet another object of the invention to provide higher confidence in alarm accuracy.

Additional features and advantages of the disclosed medical device audible and visual alarm synchronization devices, systems and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

DETAILED DESCRIPTION OF EXAMPLE EMBODIMENTS

The below disclosure relates to audible and visual alarm synchronization for medical devices, such as infusion pumps, which are used to deliver fluids (e.g., medications or nutrients) to a patient in predetermined quantities. The techniques disclosed herein synchronize the alarms (e.g., audible and visual alarms and alerts) for devices in proximity to each other. Alternatively, the alarms and alerts may purposefully be out of synchronization, for example, to assist clinicians with locating the source of an alarm or to more easily distinguish between different types of alarms/alerts. The synchronization may include synchronization (e.g., in-sync or out-of-sync) of audible alarms/alerts as well as visual alarms/alerts, such as visible light indicators.

An "alarm" or an "alert" includes any mechanism by which a signal may be generated and conveyed to a user. Alarms may include audible alarms (e.g., a sound from a speaker, a buzzer, or other sound producing device), visual alarms (e.g., an alarm message on a display such as an LCD screen, an LED, an image, etc.), tactile alarms (e.g., a vibration), and/or other mechanism. Similarly, alerts may include audible alerts (e.g., a sound from a speaker, a buzzer, or other sound producing device), visual alerts (e.g., an alert message on a display such as an LCD screen, an LED, an image, etc.), tactile alert (e.g., a vibration), and/or other mechanism. Alarms and alerts may be generated using a single mechanism or by using multiple mechanisms simultaneously, concurrently, or in a sequence. In an example, alarms and alerts may be generated using similar redundant mechanisms (e.g., two different audio alarms) or complementary mechanisms (e.g., an audio alert and a tactile alert).

Figure 1:
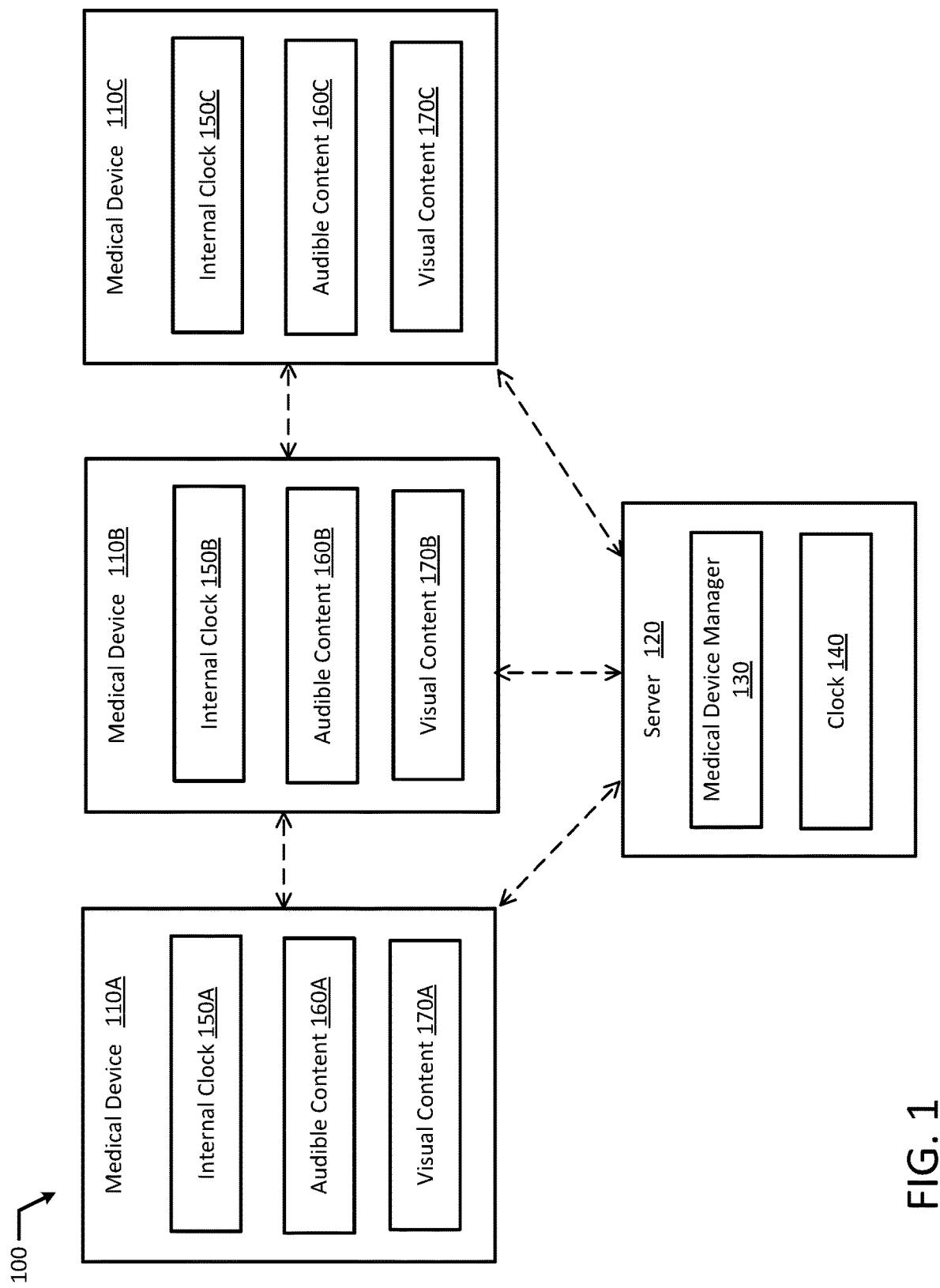
FIG. 1 is a schematic view of a system of medical devices according to an example embodiment of the present disclosure.

FIG. 1 illustrates a system 100 of medical devices 110. In the illustrated example, multiple medical devices 110A-C, such as infusion pumps, communicate with a server 120. Hereinafter, medical devices 110A-C may be referred to generally as medical device 110. The server 120 may include a medical device manager 130 to manage one or more medical device(s) 110 connected over a network. The server 120 may also include a clock 140 that serves as a master clock for the network. Each medical device 110 may include its own internal clock 150A-C and may produce audible content 160A-C (e.g., audible alerts and alarms) as well as visual content 170A-C (e.g., visual alerts and alarms).

Medical devices 110A-C may communicate with each other wirelessly or through a wired connection. The communication between medical devices 110A-C as well as communication between medical devices 110 and server 120 may include Ethernet, wireless Ethernet, a local area network, wireless local area networks, the Internet, wireless Internet, radio communications, infrared, fiber optic, and telephone communication. For example, the communication between medical devices 110 and/or server 120 may be wireless or may be hardwired communication.

Each medical device 110 may include a serial port or other I/O port connected to another device with conventional non-wireless transmission medium such as twisted-pair wire, coaxial cable, fiber optic cable, or the like. For example, multiple medical devices, such as infusion pumps, may be connected to a rack or a hub that connects multiple medical devices 110 to a serial communication link, which is connected wirelessly to a network (e.g., server 120). Additionally, each medical device 110 may include wireless communication interfaces to communication with other medical devices 110 and/or server 120.

Both the medical devices 110 and server 120 are configured to send and receive data (e.g., time data or alarm/alert data) to and from one another. For example, one medical device 110A may send alarm/alert data to another medical device 110B such that both medical devices 110A-B produce the same alarm(s) and/or alert(s). Additionally, alarm/alert data may be provided to server 120, which may broadcast that data to multiple medical devices 110 on the network. In an example, medical device status and alarm monitoring data may be relayed to server 120 on a periodic basis. An Electronic Medical Record ("EMR") system (if implemented) may have knowledge of which medical devices 110 are associated with (e.g., serving) a specific patient. For example, the EMR may have knowledge of whether a medical device 110 is registered with other devices for the same patient. Based on the knowledge of the EMR, synchronization logic may be determined for the medical devise based on the knowledge of the EMR, for example whether to synchronize alarms for devices or to avoid synchronizing alarms.

Each medical device 110, such as an infusion pump, may communicate with server 120 to synchronize its internal clock 150A-C, hereinafter referred to generally as internal clock 150, to the clock 140 of server 120. Coordination and synchronization of audible and visual alarms/alerts may be achieved by having each medical device 110 use the same time reference. For example, the local clock or internal clock 150 of each medical device 110 connected to a network may be precisely set such that it matches the time of other internal clocks 150 and the clock 140 of the network. Synchronization is typically provided by synchronizing a local internal clock 150 of each relevant medical device 110 within a communications network (e.g., connected to server 120) to a reference time (e.g., time of clock 140 of server 120). The clock 140 of server 120 may be set to a Coordinated Universal Time or ("UTC"). The local clock or internal clock 150 of each medical device 110 may be synchronized to clock 140 using one of several known techniques, protocols, and/or systems such as the Network Time Protocol ("NTP") or simple network time protocol ("SNTP").

For example, each medical device 110 (e.g., infusion pump) may use the NTP, which synchronizes each pump's internal clock 150 to network time (e.g., time of clock 140). As discussed above, this time setting is accomplished through the NTP, which is typically implemented in modern network systems and is intended to perform this exact task very precisely. The medical devices 110 may directly communicate with an NTP server or a National Institute of Standards and Technology ("NIST") server, either of which can provide a time reference.

It should be appreciated that other synchronization techniques may be used. For example, instead of server 120, other reference systems may provide a reference source of time. For example, medical devices 110 in proximity and communication with one another may synchronize with each other. For example, medical device 110A may serve as a reference device and the internal clocks 150B-C of medical devices 110B-C may synchronize with the internal lock 150A of medical device 110A.

In other examples, time and date references from other reference systems or sources may be used to synchronize the medical devices 110. The reference systems or sources may include a radio transmitter, a satellite (e.g., GPS satellite system), a cellular telephone tower, or other signal-broadcasting source. These reference systems or sources may broadcast a reference signal, which may be received by multiple medical devices (e.g., medical devices 110A-C) or by server 120. With a GPS satellite system, each pump 110 may receive a GPS clock signal, which may be an average of various atomic clocks of satellites. Using a cellular telephone time signal (e.g., from one or more cell towers, base stations or satellites) may include a code division multiple access "CDMA" clock. Similarly, medical device 110 may synchronize their time with hubs or other computers on the network. In an example, a medical device 110 may be connected to the hub or computer using a wired connection or a wireless connection, such as a Bluetooth connection, between the medical device 110 and the computer.

Synchronization or the transmission of time and date references may be achieved by transmitting high frequency light pulses, which may be emanated from overhead light sources. For example, "LiFi" may be used which is a mobile wireless technology that uses light rather than radio frequencies to transmit data. For example, LiFi uses direct modulation similar to that of infrared communication devices. Overhead light sources, such as LED light bulbs have high intensities and are capable of transmitting information at large data rates. LiFi may also be used to track medical devices 110. For example, each overhead light may be associated with an identifier (e.g., ID number) and each medical device 110 may have a light receiver that is configured to decode the identifier.

In other examples, synchronization may be implemented by using a microphone and sound processing within a medical device 110 to scan the environment for similar tones that are above a certain threshold. If a medical device 110 recognizes a similar alarm within the device's proximity, the medical device 110 may synchronize its alarm (e.g., alarm of the same type) with the detect alarm. By synchronizing alarms of the same type, the medical devices 110 may enhance the sound or visual quality of the alarm while also reducing the total amount of time the alarm is initiated for, which helps reduce the interference effects of the alarm on other alarms/alerts. Additionally, synchronizing the alarms may provide a more "harmonious" environment that is less annoying for both a clinician and patient. If the medical device 110 recognizes a different type of alarm sounding at the same time as its own alarm, the medical device 110 may adjust the frequency of its alarm such that it is out-of-sync with alarms of a different type from other medical devices. Adjusting the frequency of the alarm include adjusting how often the alarm sounds. For example, alarms that are sounded more frequently will have a smaller period (e.g., frequency of 4 times per minute and a period of 15 seconds). Providing alarms out-of-sync may advantageously improve the detectability of the different alarms by a patient or clinician. In an example, medical devices 110 that use a common backplane (e.g., multiple infusion pumps in a rack) may use the local pump-to-pump communication bus ("CAN") to trigger alarm tones. The pumps in the rack may use the wired CAN network to perform time synchronizations and communicate with each other regarding alarm synchronizations.

Synchronizing an internal clock 150 with the clock 140 of server 120 or via another external reference system or source enables each medical device 110 to have an internally stored reference time that matches other medical devices 110 on the network. This reference time may be updated periodically with the server 120 or other reference source. By updating and maintaining the internal time of each medical device 110, each medical device 110 may provide coordinated alarm and alert signals according to a specified synchronization scheme.

Furthermore, periodically synchronizing internal clocks 150 with clock 140 of server 120 or via another external reference advantageously maintains accurate time and date information even in the event of a power interruption. In the event of a power interruption or power failure (e.g., battery replacement or battery depletion) or in the event of introducing a new medical device 110 to the network, the medical devices 110 and server 120 may communicate with to accurately update the internal reference time and date.

After the clocks 150 are synchronized, the medical devices 110 may be configured for synchronous alarms/alerts or asynchronous alarms/alerts with other nearby medical devices 110. In an example, a medical device 110A may be set in synchronous mode with another medical device 110B. Additionally, medical device 110A may be set in asynchronous mode with another medical device 110C in the network. In other examples, specific alerts or alarms may be set to a synchronous mode while other alerts/alarms are set to asynchronous mode with other medical devices 110 in the network.

In the asynchronous mode, alert or alarm signals can be transmitted at arbitrary times or at coordinated times such that the alerts/alarms are out-of-sync at a predetermined interval or frequency. As discussed above, the frequency of the alert/alarm describes adjusting how often the alter/alarm sounds. For example, it may be advantageous to have alarms of different types occur out-of-sync to reduce interference so the alarms may be more easily detected or discernable by a clinician from other alarms occurring in the same proximity (e.g., same room). Additionally, out-of-sync alarms may assist with identifying the location of the same type of alarm (e.g., different infusion pumps with the same type of alarm, but in different hospital rooms). In the synchronous mode, alert or alarm signals are transmitted in accordance with a specified synchronization scheme. Providing alarms of the same type in a synchronized manner advantageously amplifies the tone of the alarm of the visual presence of the alarm.

When synchronizing alarms of the same type, the tone is advantageously amplified due to the synchronization (e.g., constructive interference). When ensuring alarms of different types are provided out-of-sync, those alarms are easier to distinguish from one another. Additionally, when synchronizing alarms, the alarms may sound more harmonious and improve the overall sound environment, for example, by sounding similar alarms at the same time, without constantly annoying patients with the same alarm from multiple pumps occurring out of sync. Furthermore, by synchronizing alarms of the same type of purposefully making alarms of different types out-of-sync, the ability to pinpoint the location of the alarm from a further distance is advantageously improved. For example, different hospital rooms may have different alarm intervals.

Typically, when an alarm event is brought up on a medical device 110, the medical device 110 may sound the alarm tone immediately so the clinicians are advantageously alerted right away. After the first or second alarm tone and while the alarm state is still active, the medical device 110 sounds the alarm at pre-defined (hard-coded) time intervals for the duration of that alarm of that type. For example, a low battery alarm may sound at every $15^{th}$ and $45^{th}$ second in a minute, and a completed infusion alarm may sound every $0^{th}$, $20^{th}$, and $40^{th}$ second in a minute. In an example, the alarm tone can register to an alternative time interval if one of the previously mentioned scenarios are present.

Instead of sounding alarms at pre-defined (hard-coded) time intervals, the medical devices 110 may sound alarms/alerts or display alarms/alerts in response to a signal received from the server 120. For example, the server may transmit an initiation signal, similar to a "heartbeat", to each medical device 110 on the network indicating when each device 110 should provide an alarm or an alert. In such implementations, the signal is received and processed by the individual medical devices 110 at approximately the same time, and the alarm/alert content would be provided in a synchronized manner as a result.

Additional methods of determining at what time interval (e.g., period) or how often (e.g., frequency) to sound alarms may include contacting an Electronic Medical Record ("EMR") system (if implemented) to determine whether the medical device 110 is registered with other devices for the same patient. The medical devices 110 registered for the same patient may be synchronized to optimize the alerts and alarms provided by those devices. For example, some of the devices or certain types of the alarms/alerts for those devices may be configured to be in-sync while other devices or types of alarms may be configured to be out-of-sync. Additionally, location services may be used to determine the proximity of a medical device 110 to other devices. Based on the proximity of devices, some devices may be synchronized if they are in the same room or may be placed out-of-sync with devices in other rooms. In some embodiments, each medical device 110 may have a different synchronization schedule. For example, some medical devices 110 may request synchronization at a first predetermined interval while other medical devices 110 request synchronization at a second predetermined interval. The interval of synchronization may depend on the type of medical device 110, location of the medical device, etc. Synchronization may occur when an alarm or an alert is triggered or at a predetermined interval such as every hour, every day, every two days, every 5 days, etc.

The device time may be synchronized via NTP periodically to offset for any drift. In an example, the amount of drift between medical devices 110 may be limited to a threshold amount. The threshold amount of drift may be set to a value that is lower than the alarm/alert period. For example, the drift may be limited to 5 percent of the alarm/alert signal period (e.g., if an alarm is sounded every 10 seconds, the difference of 0.5 seconds among the medical devices 110 may be acceptable or negligible. Other threshold amounts of drift may be used to reduce the amount of drift between devices 110 before requiring a subsequent synchronization.

In an example, alarms that are synchronized may also be set to a higher or lower priority level. For instance, if a patient is connected to multiple infusion pumps (e.g., five infusion pumps) and a downstream occlusion alarm is triggered in each of the infusion pumps, then there is a high likelihood that the pumps have accurately detected a downstream occlusion. These downstream occlusion alarms may be synchronized and set to a "high" priority alarm based on the high confidence level of the alarm. Conversely, if only a single infusion pump of the five infusion pumps had a downstream occlusion alarm triggered, the confidence in the accuracy of that alarm may be lower and the alarm may sound at a lower priority than "high" priority. In another example, other forms of alerts/alarms may be implemented such as a spoken audible alert in addition to the alarm tones when confidence is high. An example audible alert may be "please check your IV line to make sure it is not pinched."

Alerts/alarms may have different priority levels such as "low", "medium", and "high" priority. Certain types of alarms may have a default priority level. For example, a lower battery alert may be initially set to "medium" priority while a rack of infusion pumps with multiple downstream occlusion alarms may be set to a "high" priority level. The priority level may also be a determining factor in how quickly an alarm is synchronized with another alarm of the same type. For example, "low" priority alarms may wait several alarm cycles before synchronizing. Conversely, "high" priority alarms may synchronize immediately to improve their detectability.

Figure 2:
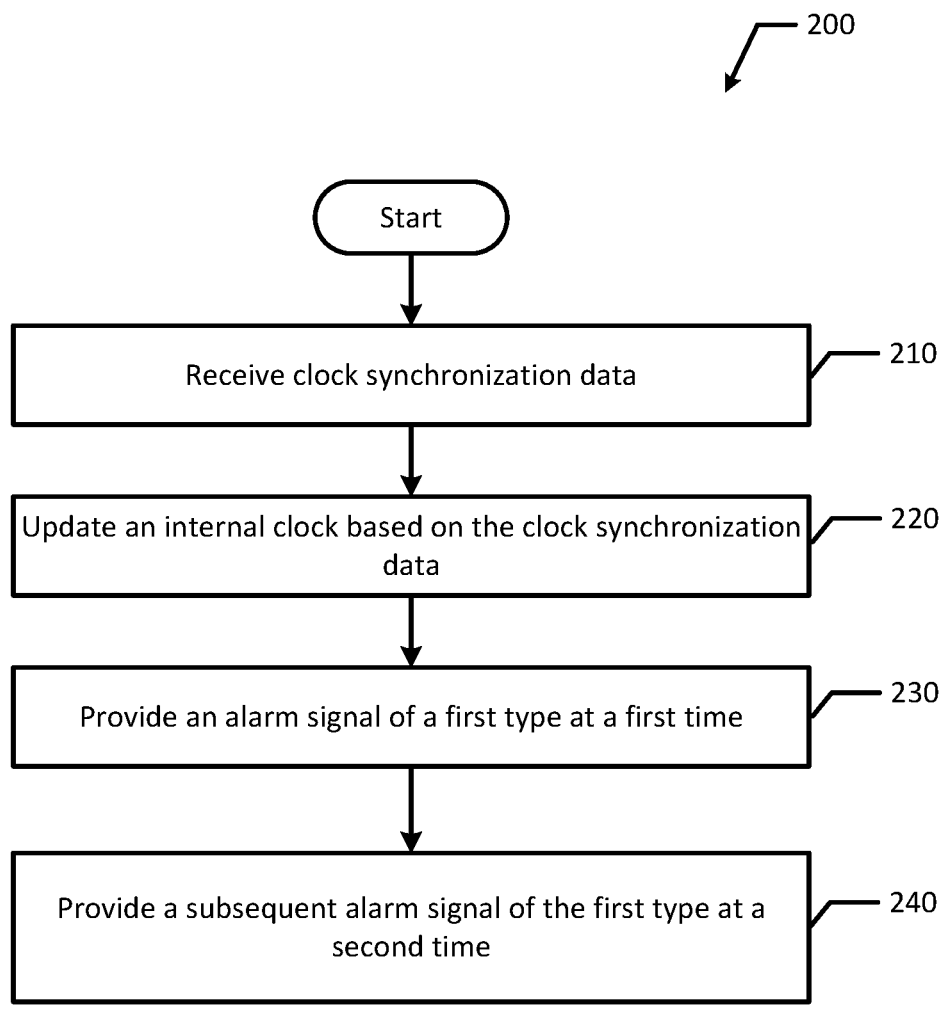
FIG. 2 illustrates a flowchart of an example process for synchronizing alarms according to an example embodiment of the present disclosure.

FIG. 2 illustrates a flowchart of an example method 200 for audible and visual alarm synchronization for medical devices in accordance with an example of the present disclosure. Although the example method 200 is described with reference to the flowchart illustrated in FIG. 2, it will be appreciated that many other methods of performing the acts associated with the method 200 may be used. For example, the order of some of the blocks may be changed, certain blocks may be combined with other blocks, blocks may be repeated, and some of the blocks described are optional. The method 200 may be performed by processing logic that may comprise hardware (circuitry, dedicated logic, etc.), software, or a combination of both.

In the illustrated example, method 200 includes receiving clock synchronization data (block 210). For example, a medical device 110 may receive clock synchronization data from a server 120. In other examples, clock synchronization data may be provided from another source, such as another medical device 110 or from another remove source (e.g., computer, GPS, cellular network, etc.). Method 200 also includes updating an internal clock based on the clock synchronization data (block 220). For example, the medical device 110 may update its internal clock 150 based on the clock synchronization data.

Then, the method 200 includes providing an alarm signal of a first type at a first time (block 230). Alarms may differ in "type" based on alarm priority (e.g., a high priority alarm is a different type than a low priority alarm), the reason for the alarm (e.g., an occlusion alarm is a different type than a low battery alarm), the device sounding the alarm (e.g., two different models of medical devices sounding an occlusion alarm may be considered alarms of different types), etc. For example, an alarm event may occur and the medical device 110 may sound an alarm tone or provide a "blinking" alarm signal immediately. Method 200 also includes providing a subsequent alarm signal of the first type at a second time (block 240). After initially providing the alarm signal, subsequent alarm signals may be provided at a second time that occurs at a predetermined interval from the first time. For example, the second time may be a time that causes the alarm signal to be in-sync with alarms of the same type (e.g., alarms from other devices). In another example, the second time may be a time that causes the alarm signal to be out-of-sync with alarms of different types from other devices such that the alarm does not negatively interfere with the other types of alarms.

Figure 3:
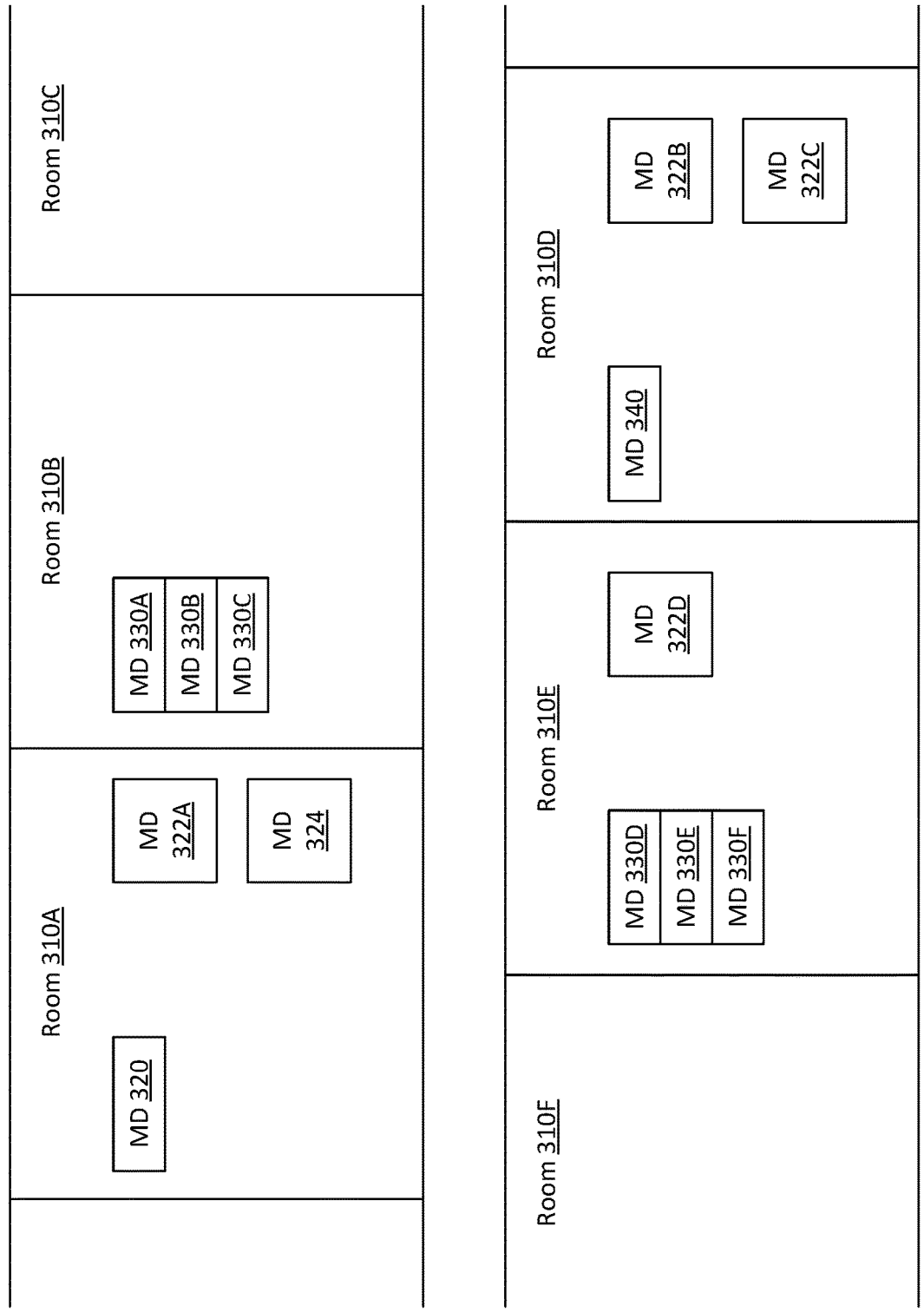
FIG. 3 illustrates a schematic view of a hospital environment according to an example embodiment of the present disclosure.

FIG. 3 illustrates a schematic view of a hospital environment according to an example embodiment of the present disclosure. In an example, a patient in room 310A may be connected to various medical devices (e.g., MD 320, MD 322A and MD 324). If an alert/alarm starts sounding on MD 320 and later another type of alarm starts sounding on MD 322A, the respective alerts/alarms may purposefully be set such that the alert/alarm from MD 320 is out of synchronization with the alert/alarm from MD 322A, which may advantageously aid in detecting each of the different types of alarms.

A patient in room 310B may be connected to three medical devices (e.g., MD 330A-C), for example, infusion pumps. When an alarm is triggered on MD 330A, to improve the detectability of the alarm, the same alarm may sound on MD 330B and/or MD 330C in a synchronized manner along with MD 330A. Additionally, if the same type of alarm is triggered on more than one of the medical devices 330A-C, the alarm may also be upgraded to a higher priority such that it sounds at a louder tone and sounds more frequently.

Around the same time, another patient in room 310E may be similarly connected to three medical devices (e.g., MD 330D-F), such as a set of infusion pumps arranged in a rack. These infusion pumps (e.g., MD 330D-F) may be same type of infusion pumps (e.g., MD 330A-C) that are in room 310B. If the same type of alarm is triggered on one of the medical devices (e.g., MD 330E) in room 310E as the alarm triggered in room 310B, the alarms may be offset such that they are sounded out of sync. For example, the alarm from room 310B may be sounded at every 0th and 30th second in a minute while the alarm from room 310E is sounded at every 15th and 45th second in the minute, which advantageously allows a doctor to distinguish and quickly locate which room the alarm is sounding from.

The different types of alerts/alarms from medical devices 320, 322A-D, 324, 330A-F and 340 from rooms 310A-F may be synchronized such that the alerts/alarms are in-synch or out-of-synch to enhance the hospital environment by reducing constant alarm noise while also minimizing interference between different alarms, reducing the stress to the patient and/or other visitors, indicating a higher confidence in alarm accuracy, improving alarm identification and detectability, improving alarm location detectability, etc.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention claimed is:

1. A system comprising:
a server including a clock; and
a plurality of medical devices in network communication with the server, wherein each medical device includes at least one alarm mechanism and an internal clock, and wherein a first medical device is configured to:
receive a clock synchronization data from the server,
update the internal clock of the first medical device based on the clock synchronization data,
determine an alarm signal to be generated is of a first type among a plurality of types of alarm signals, each type of alarm signal being associated with a predetermined interval of time,
provide the alarm signal of the first type at a first time, and
provide a subsequent alarm signal of the first type at a second time, wherein the second time occurs at a predetermined interval from the first time, wherein the predetermined interval is determined in part by the type of alarm signal, and wherein the second time is the same time the alarm signal of the first type is provided by a second medical device of the plurality of medical devices.

2. The system of claim 1, wherein the medical device is an infusion pump.

3. The system of claim 1, wherein a third medical device of the plurality of medical devices is configured to:
receive the clock synchronization data from the server,
update the internal clock of the third medical device based on the clock synchronization data,
determine a second alarm signal to be generated is of a second type among the plurality of types of alarm signals,
provide the second alarm signal of the second type at a third time to a user or a clinician associated with the medical device, and
provide a subsequent second alarm signal of the second type at a fourth time, wherein the fourth time occurs at a predetermined interval such that the subsequent second alarm signal of the second type is out-of-sync with the alarm signal of the first type from the first medical device and the second medical device.

4. The system of claim 1, wherein clock synchronization data is provided through the Network Time Protocol (NTP).

5. The system of claim 1, wherein the alarm signal is one of an audible alarm, a visual alarm, and a tactile alarm.

6. The system of claim 5, wherein the audible alarm is provided by a speaker.

7. The system of claim 5, wherein the visual alarm is provided by an LCD display.

8. The system of claim 5, wherein the visual alarm is provided by a LED.

9. An infusion pump comprising:
an internal clock;
a display device configured to provide visual content;
a speaker configured to provide audible content; and
a processor in communication with the display and the speaker, the processor configured to:
receive clock synchronization data from one of a server and another medical device,
update the internal clock based on the clock synchronization data,
determine an alarm signal to be generated is of a first type among a plurality of types of alarm signals, each type of alarm signal being associated with a predetermined interval of time,
provide the alarm signal at a first time from at least one of the display device and the speaker, and
provide a subsequent alarm signal at a second time, wherein the second time occurs at a predetermined interval from the first time, and wherein the second time is the same time the alarm signal is provided by another infusion pump.

10. The infusion pump of claim 9, wherein clock synchronization data is provided through the Network Time Protocol (NTP).

11. The infusion pump of claim 9, wherein the processor provides the alarm signal via the display device.

12. The infusion pump of claim 9, wherein the processor provides the alarm signal via the speaker.

13. The infusion pump of claim 9, wherein the processor is further configured to:
provide an alarm signal of a second type at a third time, and
provide a subsequent alarm signal of the second type at a fourth time, wherein the fourth time occurs at a predetermined interval such that the subsequent alarm signal of the second type is out-of-sync with the alarm signal of the first type.

14. A method comprising:
receiving, by a medical device, clock synchronization data from a reference source;
updating, by the medical device, an internal clock based on the clock synchronization data;
determining, by the medical device, an alarm signal to be generated is of a first type among a plurality of types of alarm signals, each type of alarm signal being associated with a predetermined interval of time,
providing, by the medical device, the alarm signal of the first type at a first time; and
providing, by the medical device, a subsequent alarm signal of the first type at a second time, wherein the second time occurs at a predetermined interval from the first time, and wherein the second time is the same time the alarm signal is provided by another medical device of the plurality of medical devices.

15. The method of claim 14, further comprising:
receiving, by a second medical device, the clock synchronization data from the server;
updating, by the second medical device, an internal clock of the second medical device based on the clock synchronization data;
determining, by the second medical device, a second alarm signal to be generated is of a second type among the plurality of types of alarm signals,
providing, by the second medical device, the second alarm signal of the second type at a third time; and providing, by the second medical device, a subsequent second alarm signal of the second type at a fourth time, wherein the fourth time occurs at a predetermined interval such that the subsequent second alarm signal of the second type is out-of-sync with the alarm signal of the first type.

16. The method of claim 14, wherein clock synchronization data is provided through the Network Time Protocol (NTP).

17. The method of claim 14, wherein the alarm signal is one of an audible alarm, a visual alarm, and a tactile alarm.

18. The method of claim 17, wherein the audible alarm is provided by a speaker.

19. The method of claim 17, wherein the visual alarm is provided by an LCD display.

20. The method of claim 17, wherein the visual alarm is provided by a LED.

* * * * *